(12) United States Patent
Costello

(10) Patent No.: US 9,610,178 B2
(45) Date of Patent: Apr. 4, 2017

(54) PROSTHETIC LIMB HEATING APPARATUS

(71) Applicant: Costello Prosthetic Warmers LLC, Liverpool, NY (US)

(72) Inventor: Bryan Costello, Liverpool, NY (US)

(73) Assignee: Costello Prosthetic Warmers LLC, Liverpool, NY (US)

( * ) Notice: Subject to any disclaimer, the term of this patent is extended or adjusted under 35 U.S.C. 154(b) by 0 days.

(21) Appl. No.: 14/449,311

(22) Filed: Aug. 1, 2014

(65) Prior Publication Data

US 2016/0030205 A1 Feb. 4, 2016

(51) Int. Cl.
*A61F 2/78* (2006.01)
*A61F 2/80* (2006.01)
*A61F 7/00* (2006.01)

(52) U.S. Cl.
CPC ...... *A61F 2/7812* (2013.01); *A61F 2002/802* (2013.01); *A61F 2007/0051* (2013.01)

(58) Field of Classification Search
CPC ...... A61F 2/70; A61F 2/78; A61F 2/80; A61F 2002/7665; A61F 2002/7875; A61F 2002/802; A61F 2002/805; A61F 2002/807; A61F 2007/0292
See application file for complete search history.

(56) References Cited

U.S. PATENT DOCUMENTS

| 2003/0039798 | A1* | 2/2003 | Meyer | B29C 45/14631 428/66.7 |
| 2007/0021841 | A1* | 1/2007 | Al-Temen | A61F 2/54 623/25 |
| 2007/0168045 | A1* | 7/2007 | Slemker | A61F 2/5046 623/34 |
| 2010/0204805 | A1* | 8/2010 | Bomkamp | A61F 2/80 623/36 |

(Continued)

FOREIGN PATENT DOCUMENTS

JP 11297627 A * 10/1999

OTHER PUBLICATIONS

Ficociello, John. A heat generating socket. Orthotics and Prosthetics, vol. 31 No. 3 p. 41-43. Sep. 1977.*

(Continued)

*Primary Examiner* — Thomas J Sweet
(74) *Attorney, Agent, or Firm* — Dennis B. Danella, Esq.; Woods Oviatt Gilman LLP

(57) ABSTRACT

A prosthetic limb heating apparatus for use with a prosthetic assembly includes a housing having a side wall that defines open upper and lower ends. The upper end is configured to receive an upper limb portion and prosthetic socket into the housing. The open lower end is configured to allow the upper limb portion to pass therethrough but not the prosthetic socket such that the prosthetic socket is nested in the interior area. An electrically conductive wire is situated on the housing and extends circuitously thereabout, the con- (Continued)

ductive wire having opposed first and second ends. A battery is coupled to the side wall of the housing and electrically connected to the first and second ends of the conductive wire so as to selectively energize the conductive wire. The conductive wire imparts heat to the prosthetic socket when the socket is nested within the housing and the conductive wire is energized.

20 Claims, 7 Drawing Sheets

(56) References Cited

U.S. PATENT DOCUMENTS

| | | | |
|---|---|---|---|
| 2012/0004738 A1* | 1/2012 | Westrate | A61F 2/78 623/36 |
| 2013/0079893 A1* | 3/2013 | Allemand | A61F 2/7812 623/36 |

OTHER PUBLICATIONS

Harvey, Zach. OandP listserve responsese to socket warmers. Oandp.com Feb. 8, 2014.*
Tremblay, Gary. Heat Pads for TR Socket. OandP Listserve. Oandp.com Dec. 10, 2012.*
Derwent abstract of CN202842520U. Zhou, Y. Apr. 3, 2013. A43B7/04.*
C. Woodford, "Prosthetics: A Simple Introduction to Artificial Limbs," http://www.explainthatstuff.com/prosthetic-artificial-limbs.html, Last Updated: Nov. 12, 2015.
"Check Socket Fitting—Care Manuals—Advanced Prosthetics," http://advancedprosthetics.opmarketing.com/patients/catalog/transfemoral-patient/temporary-prosthesis, 2016.

* cited by examiner

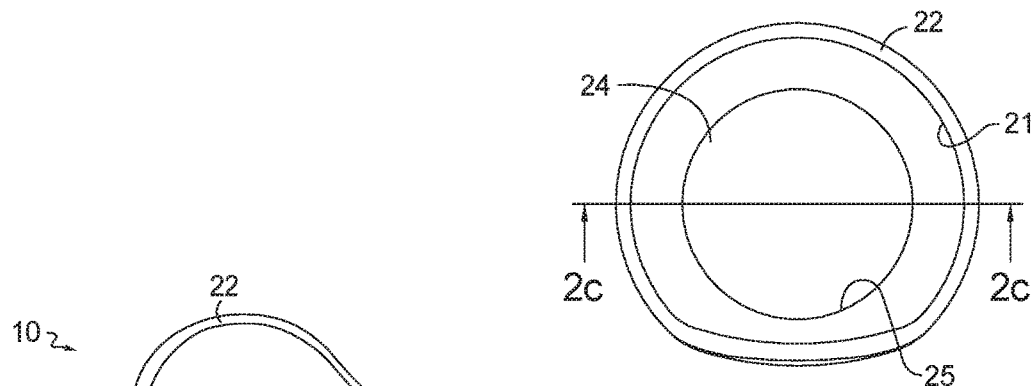
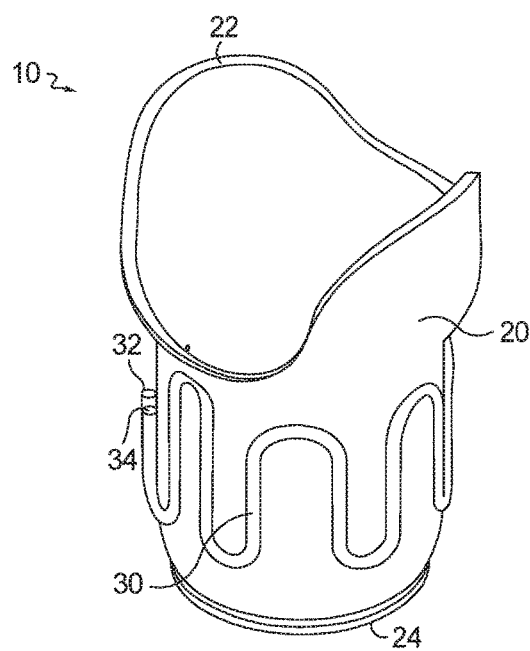
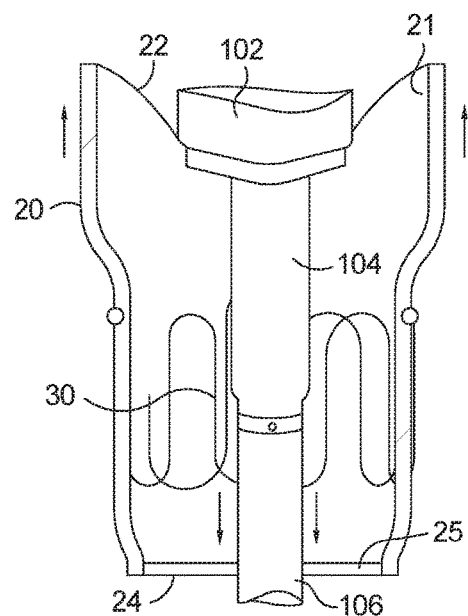
FIG. 2b.
FIG. 2a.
FIG. 2c.

PROSTHETIC LIMB HEATING APPARATUS

BACKGROUND OF THE INVENTION

This invention relates generally to heating devices and, more particularly, to a prosthetic limb heating apparatus configured to impart heat to a liner of a prosthetic limb assembly such that the stump of an amputee is warmed when a conductive wire of the prosthetic limb heating apparatus is energized.

Persons who have experienced the amputation of a limb, such as a leg or an arm, must care for stump that is left, including addressing the discomfort that occurs when the stump gets cold. An amputee's stump may get cold due to decreased blood circulation or due to interaction with a prosthetic device that is pulled on over the stump.

Various devices and proposals have been introduced in an attempt to keep an anatomical stump warm, such as wearing tube socks over the stump. In US 2012/0004738, it was proposed that a warming sleeve include a heated wire powered by a rechargeable battery. Although assumably effective for its intended purpose, the proposed heated sleeve has the potential to burn the person wearing it as it is in direct contact with the stump. In addition, the warming sleeve has a closed lower end such that it cannot be worn while the amputee is actually wearing a prosthetic assembly, such as an artificial arm or leg worn by the amputee. In other words, the heated sleeve does not allow portions of a prosthetic assembly to extend therethrough.

Therefore, it would be desirable to have a prosthetic limb heating apparatus having a sleeve that defines an open top and open bottom such that a traditional prosthetic assembly may still be worn in a normal fashion. Further, it would be desirable to have a prosthetic limb heating apparatus configured to receive a prosthetic liner therein and that warms the liner such that the liner that receives a stump of an amputee is heated.

SUMMARY OF THE INVENTION

A prosthetic limb heating apparatus according to the present invention for use with a prosthetic assembly having a upper limb portion extending away from a prosthetic liner and having a lower limb portion operatively coupled to the upper limb portion includes a sleeve having a continuous side wall that defines an interior area, an open upper end, and an open lower end. The open upper end of the sleeve is configured to receive the upper limb portion and prosthetic liner into the interior area. The open lower end of the sleeve is configured to allow the upper limb portion to pass therethrough and to prevent the prosthetic liner from passing therethrough such that the prosthetic liner is nested in the interior area. An electrically conductive wire is situated on the sleeve and extends circuitously thereabout, the conductive wire having opposed first and second ends.

A battery is operatively coupled to the side wall of the sleeve, the battery being electrically connected to the first and second ends of the conductive wire so as to selectively energize the conductive wire. The conductive wire is configured to impart heat to the prosthetic liner when the prosthetic liner is nested within the interior area of the sleeve and the conductive wire is energized.

Therefore, a general object of this invention is to provide a prosthetic limb heating apparatus having a sleeve that receives the components of a prosthetic limb assembly into an interior space wherein they are selectively heated.

Another object of this invention is to provide a prosthetic limb heating apparatus, as aforesaid, having a sleeve that defines an open top and open bottom such that a traditional prosthetic assembly may still be worn in a normal fashion.

Still another object of this invention is to provide a prosthetic limb heating apparatus, as aforesaid, that is configured to receive a prosthetic liner therein and that warms the liner such that the liner that receives a stump of an amputee is heated.

Yet another object of this invention is to provide a prosthetic limb heating apparatus, as aforesaid, in which a sleeve is wrapped with an electrical wire that heats the sleeve when energized by a battery.

A further object of this invention is to provide a prosthetic limb heating apparatus, as aforesaid, that is easy to use and economical to manufacture.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 1b is an exploded view of the heating apparatus as in FIG. 1a;

FIG. 2a is a perspective view of the heating apparatus removed from use with the assembly as in FIG. 1a;

FIG. 2b is a top view of the heating apparatus as in FIG. 2a;

FIG. 2c is a sectional view taken along line 2c-2c of FIG. 2b;

FIG. 3b is an exploded view of the heating apparatus as in FIG. 3a;

FIG. 5b is a top view of the battery housing as in FIG. 5a;

FIG. 5c is a rear view of the battery housing as in FIG. 5a;

FIG. 6b is an exploded view of the sleeve and assembly of FIG. 6a; and

DESCRIPTION OF THE PREFERRED EMBODIMENT

A prosthetic limb heating apparatus for use with a prosthetic limb assembly of an amputee will now be described in detail with reference to FIG. 1a to 7 of the accompanying drawings. The prosthetic limb heating apparatus 10 includes a sleeve 20 (i.e., a housing) configured to receive a prosthetic liner 102 (i.e., a socket) of a prosthetic limb assembly and a conductive wire 30 situated to impart heat to the sleeve 20 when energized.

Figure 1A:
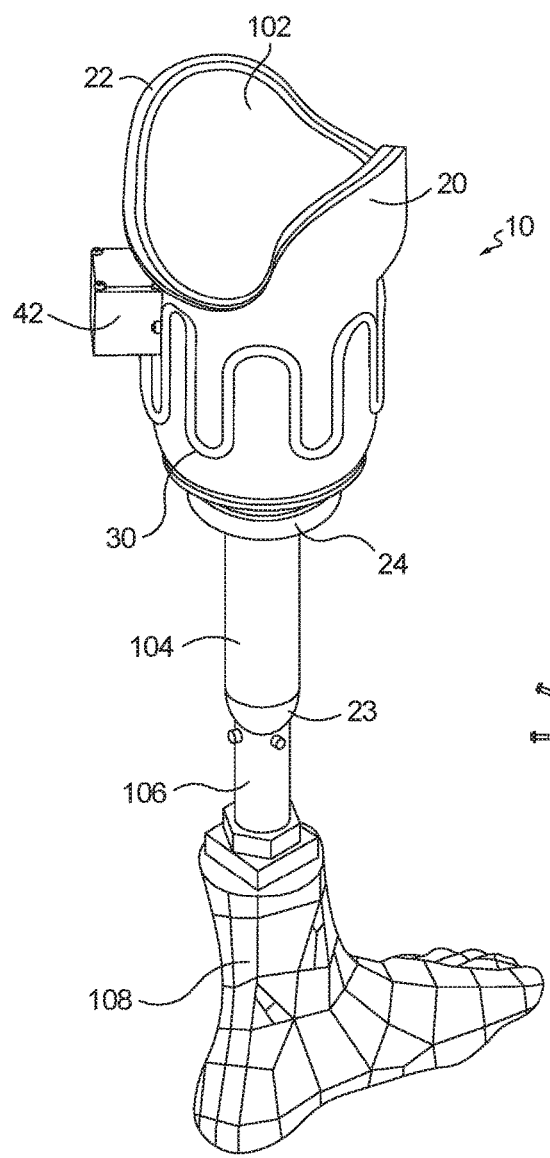
FIG. 1a is a perspective view of a prosthetic limb heating apparatus according to a preferred embodiment of the present invention illustrated in use with a prosthetic limb assembly.
Figure 1B:
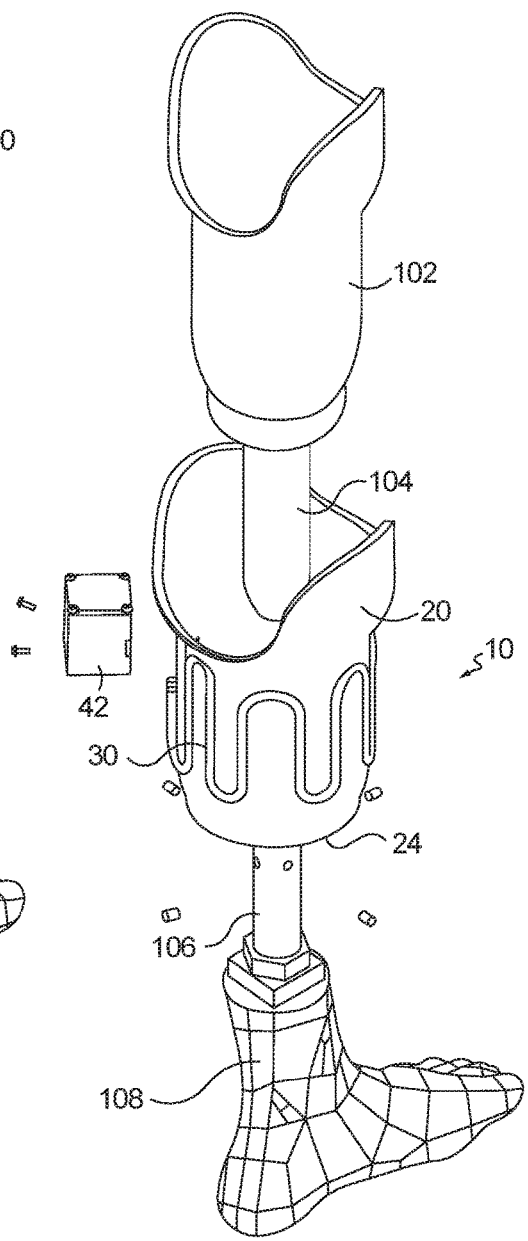
Figure 6A:
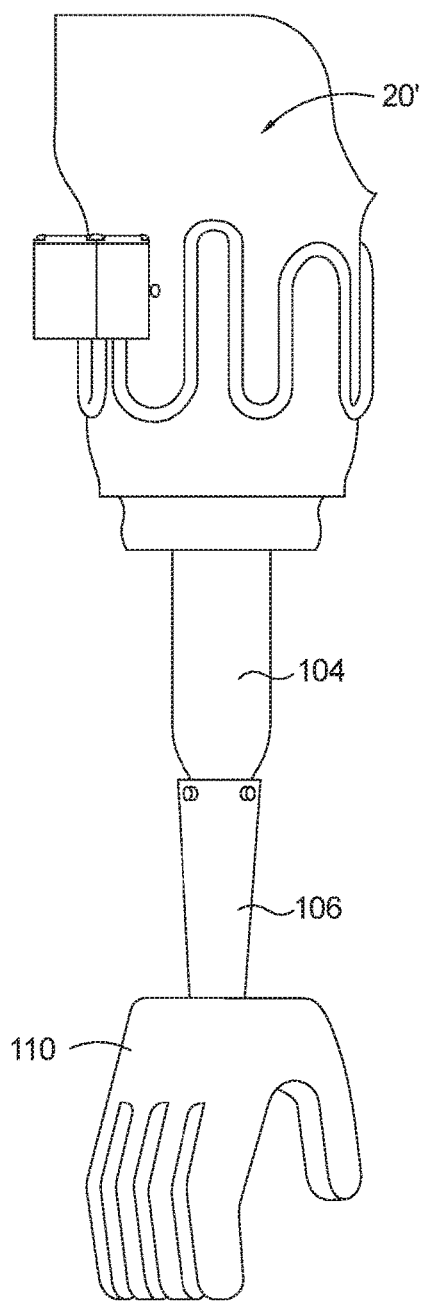
FIG. 6a is a side view of a sleeve of the heating apparatus configured for use with an arm prosthetic assembly.
Figure 6B:
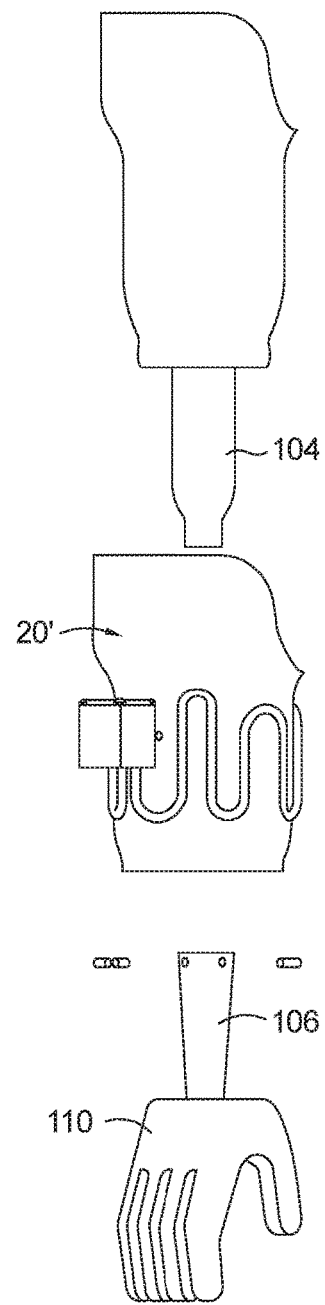

A typical prosthetic limb assembly includes prosthetic liner 102 which surrounds an amputated stump of an individual who has lost a limb such as a portion of a leg or arm. As shown in FIG. 1b and 6b, the prosthetic liner 102 can be pulled onto the stump at the end of a person's leg or arm after an amputation. The prosthetic limb assembly may also include an upper limb connector portion 104 extending from a lower end of the prosthetic liner 102, the upper limb connector portion 104 being simulative of a person's leg or arm, as the case may be. Finally, a lower limb connector portion 106 may be coupled to a lower end 23 of the upper limb connector portion 104. Finally, the prosthetic limb assembly may include an artificial foot 108 or artificial hand 110 coupled to the lower limb connector portion 106.

The sleeve 20 includes a continuous side wall having a generally cylindrical configuration. Preferably, the sleeve 20 is constructed of a rigid material, such as polypropylene or polyvinylchloride, or other plastic. The side wall of the sleeve 20 defines an open upper end 22 (i.e., brim), an opposed open lower end 24 (i.e., distal end), and an interior area between the ends. The open upper end 22 defines a first aperture 21 that is configured to receive the upper limb connector portion 104 and the prosthetic liner 102. In other words, the first aperture 21 includes a diameter that is larger than a diameter or dimension of both the upper limb connector portion 104 and prosthetic liner 102 of a prosthetic assembly. It is understood that the sleeve 20 may be used to warm an upper limb connector portion 104 associated with an amputated leg or arm.

The open lower end 24 defines a second aperture 25 that is configured to allow the upper limb connector portion 104 to extend therethrough but that does not allow the prosthetic liner 102 to pass therethrough. In other words, the second aperture 25 of the sleeve 20 has a diameter that is larger than a diameter or dimension of the upper limb connector portion 104 such that the upper limb connector portion 104 may pass completely through the lower end 24. However, the open lower end 24 of the sleeve 20 is smaller than a diameter or dimension of the prosthetic liner 102 such that it cannot pass therethrough. When the upper limb connector portion 104 has extended completely through the lower end 24 of the sleeve 20, the prosthetic liner 102 is nested within the interior area of the sleeve 20 (FIG. 1a).

In further explanation of the configuration of the sleeve 20, the side wall of the sleeve 20 may include an upper portion 26 adjacent to the open upper end 22. The upper portion 26 includes upstanding walls 27 that extend upwardly and outwardly away from the interior area of the sleeve 20 so as to guide the prosthetic liner 102 into the interior area (FIGS. 1b and 2a to 2c). Similarly, the side wall of the sleeve 20 may include a lower portion 29 adjacent the open lower end 24. The side wall of the sleeve 20 includes a middle portion sandwiched between the upper portion 26 and the lower portion 29. The upper portion 26 defines a diameter that is greater (longer) than a diameter defined by the middle portion 28. The middle portion 28 defines a diameter that is greater (longer) than a diameter defined by the lower portion 29. As described previously, the configuration of the sleeve 20 enables an upper end 22 of the prosthetic limb assembly and the prosthetic liner 102 to pass through upper and lower ends of the sleeve 20 but does not allow the prosthetic liner 102 to pass through the lower end 24. Rather, the prosthetic liner 102 is nested within the sleeve 20 and is warmed by the conductive wire 30 in the sleeve 20 when energized as will be described in more detail later.

Figure 7:
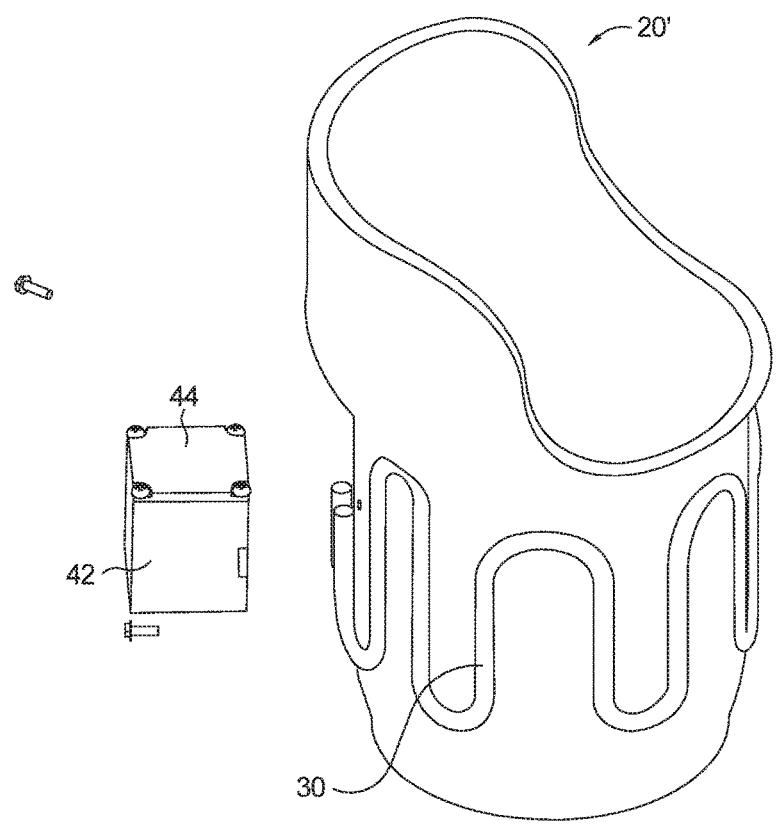
FIG. 7 is an exploded view of the sleeve and battery housing as in FIG. 6b.

In an embodiment for use with a prosthetic arm, the sleeve may include a slightly different configuration and will be referred to as sleeve 20'. The modified configuration is shown in FIGS. 6a, 6b, and 7. Specifically, the upper portion of the sleeve 20' defines an open side configured to receive a prosthetic liner for a prosthetic arm.

Figure 3A:
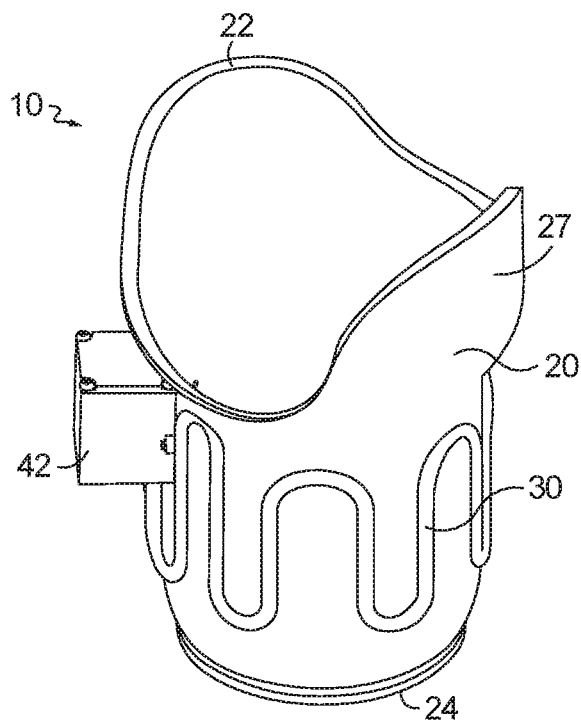
FIG. 3a is a perspective view from a different angle of the heating apparatus as in FIG. 1b.
Figure 3B:
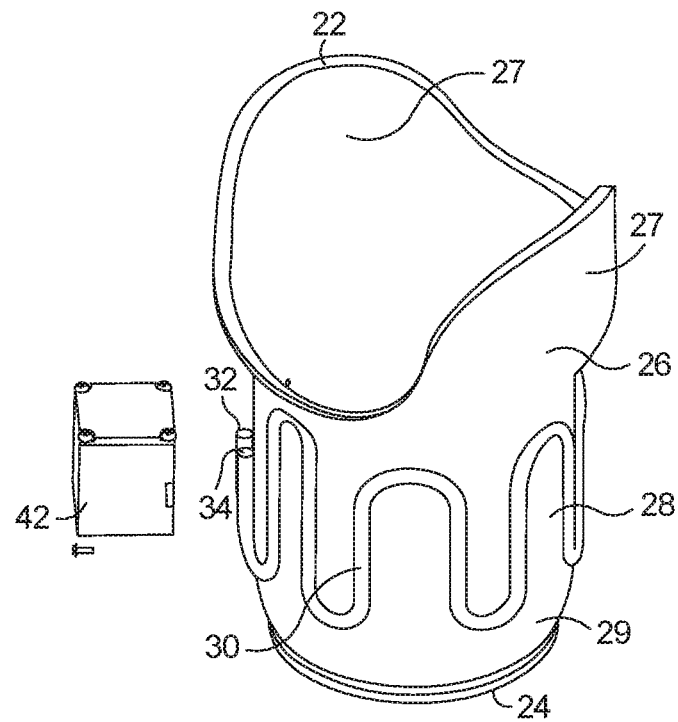

The conductive wire 30 is associated with the sleeve 20 such that the sleeve 20 is warmed when the conductive wire 30 is energized by the battery 40. More particularly, the conductive wire 30 includes a first end 32 and an opposed second end 34 that are electrically connected to the battery 40 so as to selectively conduct current in a circuit between the ends. The conductive wire 30 is positioned to loop around the entire sleeve 20 and, as a result, to impart heat to the sleeve 20 when energized. Therefore, the prosthetic liner 102 of a prosthetic limb assembly is warmed by conduction when nested within the interior area of the sleeve 20 as described above. In an embodiment, the conductive wire 30 may be arranged in a winding pattern, such as looping up and down between upper and lower ends of the sleeve 20, such that a substantial area of the sleeve 20 is covered and warmed by the conductive wire 30 when energized. In an embodiment, the conductive wire 30 may be situated on an outer surface of the sleeve 20 (FIG. 3b). In another embodiment, the conductive wire 30 may be imbedded in the sleeve 20, such in a channel formed during the molding of the sleeve 20.

Figure 4:
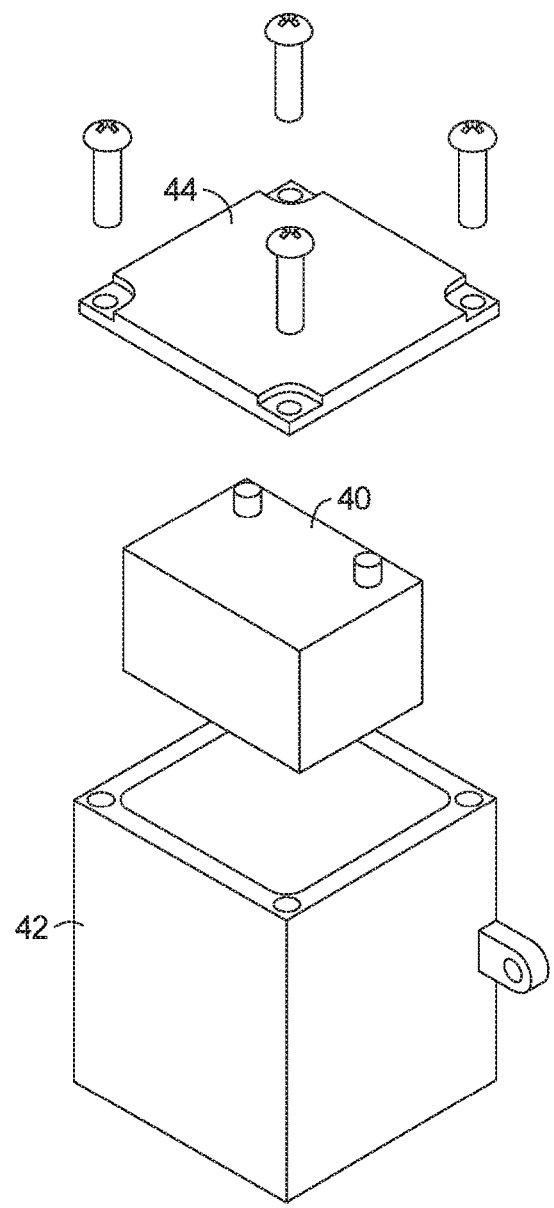
FIG. 4 is an exploded view of the battery housing as in FIG. 3b.
Figure 5A:
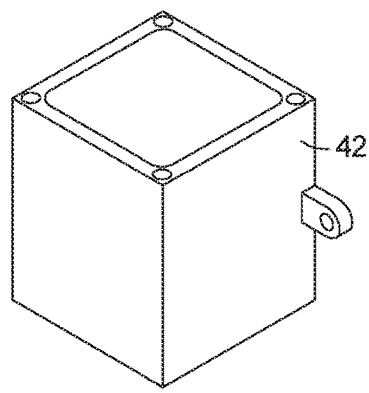
FIG. 5a is a perspective view of the battery housing as in FIG. 4.
Figure 5B:
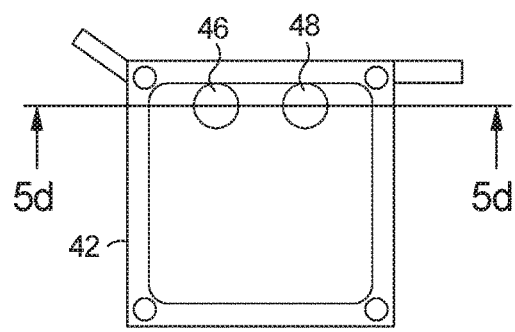
Figure 5C:
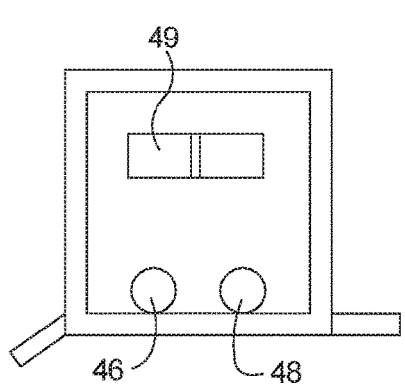
Figure 5D:
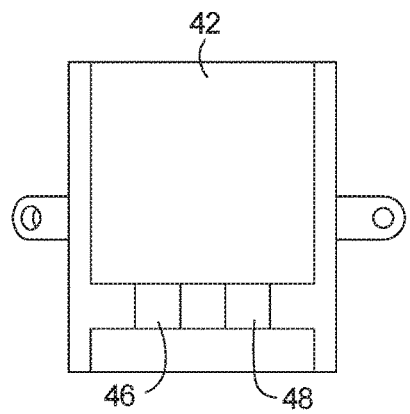
FIG. 5d is a sectional view taken along line 5d-5d of FIG. 5b.

A battery housing 42 is coupled to an outer surface of the sleeve 20. The battery housing 42 defines an interior space and the battery 40 is situated therein (FIG. 4). The first end 32 and second end 34 of the conductive wire 30 are inserted into the battery housing 42 through apertures 46 and 48 (FIGS. 5b to 5d), respectively, and electrically connected to the battery 40. The battery 40 may be selectively actuated by a switch 49, button, or the like (FIG. 5c). The battery housing 42 may include a door 44 or panel that is movable to an open configuration or is completely removable such that the battery 40 is removable and replaceable (FIG. 4).

The prosthetic limb heating apparatus 10 may be used with a traditional prosthetic limb assembly. In use, the upper limb connector portion 104 of a prosthetic limb assembly may be nested in the sleeve 20 of the prosthetic limb heating apparatus 10 by extending the upper limb connector portion 104 completely through the open lower end 24 of the sleeve 20 until the liner 102 is nested tightly in the interior space of the sleeve 20 (FIG. 1a). Then, a distal end of the upper limb connector portion 104 may be coupled to a lower limb connector portion 106 independent of sleeve 20 (i.e., the housing) in the usual manner. The battery 40 may then be actuated to deliver current to the conductive wire 30, thereby imparting heat to the sleeve 20 and, conductively, to the nested upper limb connector portion 104 and stump of a person's arm or leg, as the case may be.

It is understood that while certain forms of this invention have been illustrated and described, it is not limited thereto except insofar as such limitations are included in the following claims and allowable functional equivalents thereof.

The invention claimed is:

1. A prosthetic limb heating apparatus for use with a prosthetic assembly having a socket for receiving a residual limb, an upper limb connector portion extending from a lower end of the socket, a lower limb connector portion operatively coupled to the upper limb connector portion, and an artificial limb coupled with the lower limb connector portion, said prosthetic limb heating apparatus comprising:

a housing having a continuous side wall that defines an interior area configured to receive the socket of the prosthetic assembly, a brim, and a distal end;
wherein:
said brim of said housing defines a first aperture, wherein said first aperture is configured to receive the upper limb connector portion of the prosthetic assembly and the socket into said interior area;
said distal end of said housing defines a second aperture, wherein the upper limb connector portion of the prosthetic assembly passes completely through said second aperture and is operatively coupled with the lower limb connector portion of the prosthetic assembly independent of said housing, and wherein said second aperture is configured to prevent the socket from passing through said second aperture such that the socket is nested in said interior area;
an electrically conductive wire associated with said housing and extending circuitously thereabout, said conductive wire having opposed first and second ends; and
a battery operatively coupled to said side wall of said housing, said battery being electrically connected to said first and second ends of said conductive wire so as to selectively energize said conductive wire;
wherein said conductive wire is configured to impart heat to the socket when the socket is nested within said interior area of said housing and said conductive wire is energized, and
wherein said housing is selectively removable from the socket while the residual limb is received in the socket.

2. The prosthetic limb heating apparatus as in claim 1, comprising a battery housing coupled to said outer surface of said housing, said battery being positioned in an interior space defined by said battery housing.

3. The prosthetic limb heating apparatus as in claim 2, wherein said battery housing includes a door that is movable to an open configuration such that said battery is removable.

4. The prosthetic limb heating apparatus as in claim 1, wherein said conductive wire is arranged in a wave pattern on said outer surface of said housing, wherein said wave pattern includes a plurality of apexes, and wherein said plurality of apexes point towards said brim and said distal end of said socket.

5. The prosthetic limb heating apparatus as in claim 4, wherein said housing is constructed of plastic.

6. The prosthetic limb heating apparatus as in claim 1, wherein:
said housing includes:
an upper portion adjacent said brim;
a lower portion adjacent said distal end; and
a middle portion sandwiched between said upper portion and said lower portion;
said upper portion defines a diameter greater than a diameter defined by said middle portion; and
wherein said diameter of said middle portion is greater than a diameter defined by said lower portion.

7. The prosthetic limb heating apparatus as in claim 6, wherein said housing is constructed of plastic.

8. The prosthetic limb heating apparatus as in claim 7, wherein said upper portion of said housing includes upstanding walls that extend outwardly away from said middle portion so as to funnel the socket into said interior area of said housing.

9. The prosthetic limb heating apparatus as in claim 6, wherein said housing is constructed of a rigid material.

10. The prosthetic limb heating apparatus as in claim 9, wherein said conductive wire is imbedded in said housing.

11. The prosthetic limb heating apparatus as in claim 10, wherein said upper portion of said housing includes upstanding walls that extend outwardly away from said middle portion so as to selectively funnel the socket into said interior area of said housing.

12. The prosthetic limb heating apparatus as in claim 6, wherein said conductive wire is imbedded in said housing.

13. The prosthetic limb heating apparatus as in claim 6, wherein said conductive wire is situated on an outer surface of said housing.

14. The prosthetic limb heating apparatus as in claim 6, wherein said upper portion of said housing includes upstanding walls that extend outwardly away from said middle portion so as to funnel the socket into said interior area of said housing.

15. In combination:
a prosthetic assembly including:
a socket for receiving a residual limb, said socket including a lower end;
an upper limb connector portion extending from said lower end of said socket;
a lower limb connector portion operatively coupled to said upper limb connector portion; and
an artificial limb coupled with said lower limb connector portion; and
a prosthetic limb heating apparatus including:
a housing including a continuous side wall that defines an interior area configured to receive the socket of the prosthetic assembly, a brim, and a distal end;
wherein:
said brim of said housing defines a first aperture, wherein said first aperture receives said upper limb connector portion of the prosthetic assembly and said socket into said interior area;
said distal end of said housing defines a second aperture, wherein said upper limb connector portion of the prosthetic assembly passes completely through said second aperture and is operatively coupled with said lower limb connector portion of the prosthetic assembly independent of said housing, and wherein said second aperture prevents said socket from passing through said second aperture such that said socket is nested in said interior area;
an electrically conductive wire associated with said housing and extending circuitously thereabout, said conductive wire having opposed first and second ends; and
a battery operatively coupled to said side wall of said housing, said battery being electrically connected to said first and second ends of said conductive wire so as to selectively energize said conductive wire;
wherein said conductive wire is configured to impart heat to said socket when the socket is nested within said interior area of said housing and said conductive wire is energized, and
wherein said housing is selectively removable from the socket while the residual limb is received in the socket.

16. The combination as in claim 15, wherein said conductive wire is arranged in a wave pattern on said outer surface of said housing, wherein said wave pattern includes a plurality of apexes, and wherein said plurality of apexes point towards said brim and said distal end of said socket.

17. The combination as in claim 15, wherein:
said housing includes:
an upper portion adjacent said brim;

a lower portion adjacent said distal end; and
a middle portion sandwiched between said upper portion and said lower portion;
said upper portion defines a diameter greater than a diameter defined by said middle portion; and
wherein said diameter of said middle portion is greater than a diameter defined by said lower portion.

18. The combination as in claim 17, wherein said upper portion of said housing includes upstanding walls that extend outwardly away from said middle portion so as to funnel the socket into said interior area of said housing.

19. The combination as in claim 15, wherein said conductive wire is imbedded in said housing.

20. The combination as in claim 15, wherein said conductive wire is situated on an outer surface of said housing.

* * * * *